United States Patent [19]

Hylarides et al.

[11] Patent Number: 4,577,046

[45] Date of Patent: Mar. 18, 1986

[54] DEAMINATION OF AROMATIC AMINES

[75] Inventors: Mark D. Hylarides; Fred A. Mettler, Jr., both of Albuquerque, N. Mex.

[73] Assignee: University of New Mexico, Albuquerque, N. Mex.

[21] Appl. No.: 619,203

[22] Filed: Jun. 11, 1984

[51] Int. Cl.[4] ............................................. C07C 45/65
[52] U.S. Cl. ................................ 568/312; 562/493; 562/494; 585/469; 260/397; 558/350; 568/716; 568/937; 568/630; 570/101; 548/579; 548/127; 546/348
[58] Field of Search ...................... 562/458, 493, 494; 585/469; 568/312, 716, 937, 630; 570/101; 260/397, 465; 548/579, 127; 546/348

[56] References Cited

U.S. PATENT DOCUMENTS 2,481,922  9/1949  Hager ................................. 568/312
2,563,037  8/1951  Ipatieff et al. ...................... 568/312

OTHER PUBLICATIONS

Zollinger, Angewandte Chemie, vol. 17, pp. 141–149 (1978).
Lahoti et al., Indian J. of Chem., vol. 20B, pp. 767–769 (1981).
Zollinger, "Azo and Diazo Chemistry", pp. 93–101 (1961).
Wang et al., Chem. Abst., vol. 97, #146,196t (1982).
J. Am. Chem. Soc., 1952, vol. 74, p. 6297, Roe et al., "Replacement of the Primary Aromatic Amino Group by Hydrogen using Diazonium Fluoborates".
J. Org. Chem., 1963, vol. 28, p. 568, Rutherford et al., "Decomposition of Aryldiazonium Hexafluorophosphates in Tetramethylurea . . . ".
J. Am. Chem. Soc., 1939, vol. 61, p. 2418, Brewster et al., "Reduction of Diazonium Salts to Hydrocarbons with Alkaline Formaldehyde".
J. Org. Chem., 1977, vol. 42, p. 3494, Doyle et al., "Reduction Deamination of Arylamines by Alkyl Nitrites in N,N–Dimethylformamide . . . ".
J. Org. Chem., 1978, vol. 43, p. 4120, Doyle et al., "Alkyl Nitrite–Metal Halide Deamination Reactions, 5, In Situ Generation of Nitrosyl . . . ".
J. C. S. Perkin I, 1973, p. 541, Cadogan et al., "A Simple and Convenient Deamination of Aromatic Amines".

*Primary Examiner*—James H. Reamer
*Attorney, Agent, or Firm*—Charles W. Fallow; Martin P. Hoffman; Mitchell B. Wasson

[57] ABSTRACT

Deamination of aromatic primary amines by diazotization and hydrogen replacement of the diazo group is accelerated in the presence of hydrogen peroxide. Yields of at least about 85% are typical, with reaction times of usually about one hour or less.

23 Claims, No Drawings

DEAMINATION OF AROMATIC AMINES

BACKGROUND OF THE INVENTION

The deamination of aromatic amines is a procedure of wide application in the chemical industry. While a variety of deamination techniques are known, deamination of aromatic primary amines customarily entails activation of the primary amino group by diazotization, followed by replacement of the diazo group with hydrogen. The conversion is conveniently effected by a "one-port", "one-step" reaction, wherein the primary amine is deaminated by reaction with a source of nitrous acid such as an alkyl nitrite, in the presence of an appropriate hydrogen donor, usually a solvent such as tetrahydrofuran or dioxane, as described, for example, by Cadogan et al (*J. C. S. Perkins I,* 1973, 541–542); Doyle et al (*J. Org. Chem.* 43: 4120-25, 1979); or Doyle et al (*J. Org. Chem* 42: 3494–98, 1977). The reaction broadly involves diazotization of the aromatic amine with decomposition of the diazonium salt to an intermediate aryl radical, which accepts hydrogen from the donor according to the following scheme:

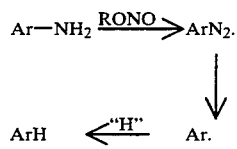

More classically, deamination is accomplished by a "one-pot," "two-step" textbook reaction, wherein the aromatic amine is first diazotized (usually by sodium nitrite in a mineral acid), and the diazo group subsequently replaced by hydrogen by reaction of the diazonium salt (generally termed "reduction" in the art) with an appropriate hydrogen donor such as alkaline formaldehyde, ethanol or hypophosphorous acid according to the following exemplary scheme:

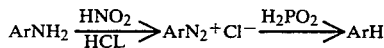

(see e.g., Brewster et al, *JACS* 61:2418-9, 1939). Simple diazonium salts may also be converted to more complex intermediate salts such as the diazonium fluoborates or fluorophosphates to improve stability and efficiency of the subsequent replacement reaction, as described, for example, in *J. Org. Chem.* 28:568-571, 1963 or *JACS* 74:6297–6298, 1952.

While these known techniques are generally effective in accomplishing the desired deamination, the reactions usually require several hours for completion, with frequently low yields. Further, the yields vary drastically and unpredictably with a number of parameters, particularly the types of hydrogen donors employed, and especially the number and type of substituents present on the aromatic moiety. It is accordingly desirable to provide an improved method for deaminating aromatic amines which is simple, versatile, reliable and rapid.

SUMMARY OF THE INVENTION

The invention comprises a method for the deamination of aromatic primary amines, wherein deamination is promoted by hydrogen peroxide. Reaction times of less than about one hour and yields of deaminated product, usually free from contaminating by-product, of at least about 85% of theoretical are typical. The reaction is amenable to both microscale and industrial scale applications.

DETAILED DESCRIPTION OF THE INVENTION

According to the invention, accelerated reaction and improved yield is obtained by conducting conventional deamination procedures with added hydrogen peroxide. Diazotization of the amine starting material to activate the amino group, and replacement of the diazo group of the diazotization product with hydrogen ("reduction") are accomplished by methods known to the prior art such as those described supra. By the process of the invention, hydrogen peroxide is employed to promote deamination by an oxidation mechanism which appears to facilitate removal of the diazo group; other strong oxidizing agents such as certain peracids may also promote removal of this group. Generally, less than molar equivalents of the oxidizing agent (i.e., less than 1 mol $H_2O_2$ per mol diazonium salt) are added at the appropriate stage of the reaction.

Preferably, a "one-pot", one-step technique is employed, and the aromatic amine reactant is combined with a suitable source of nitrous acid, $H_2O_2$, and the desired hydrogen donor. Preparation of the diazonium salt and replacement of the diazo group thus both take place in the presence of the hydrogen peroxide. Alternatively, the diazonium salt or derivative thereof is separately prepared, and $H_2O_2$ is combined with the diazonium salt and hydrogen donor in the replacement step of the reaction to promote removal of the diazo group.

A variety of aromatic amines are useful as starting materials in the process of the invention. Amines of the formula $ArNH_2$ are suitable, wherein Ar is an aryl group such as phenyl, biphenyl, anthraquinoyl, naphthyl, thiazoyl, pyridyl, pyrrolyl, or quinoyl; Ar may also be a steroid A-ring (aromatic ring). The aryl moiety may be unsubstituted or substituted with one or more conventional groups such as halo, alkyl, nitro, alkoxy, carbonyl, acyl, hydroxy, or aryl, especially phenyl. The process of the invention is particularly applicable to aromatic amines having one or more substituents in addition to the primary amino group, as, in contrast to prior art deamination processes, these substituent groups do not significantly interfere with the deamination process according to the present invention. Aromatic primary amines having more than one primary amino group, or secondary or tertiary amino substituents such a monoalkylamino of dialkylamino substituents are also suitable starting materials.

The diazonium salt is formed by reacting the aromatic amine with a source of nitrous acid, as is well-known in the art. The source of nitrous acid is usually a lower alkyl ($C_1$–$C_{10}$) nitrite in a suitable solvent, or $NaNO_2$ in a mineral acid, particularly HCl or $H_2SO_4$. If desired, the diazonium salt may be derivitized before removal of the diazo group as is common in the art, for example by reaction with an appropriate fluoboric acid such as hexafluoboric acid or tetrafluoboric acid to form the corresponding fluoborate.

After activation of the amino group by conversion into a diazonium salt or derivative thereof, the deamination reaction is completed by removal of the diazo group (or derivatized diazo group) and replacement with hydrogen in the presence of $H_2O_2$; a suitable hydrogen donor, usually a solvent for the diazonium salt, is employed as a source of hydrogen. In this reaction, useful hydrogen donors include organic solvents such as tetrahydrofuran or dioxane, while in other types of deaminations, hydrogen donors are generally alkaline formaldehyde, ethanol or hypophosphorous acid. Since unpurified dioxane may contain significant amounts of $H_2O_2$, additional $H_2O_2$ may not be necessary for good deamination when dioxane is employed as a solvent.

In a preferred embodiment of the invention, an aromatic amine of the formula $ArNH_2$ is combined with a source of nitrous acid in either dioxane or tetrahyrofuran, and hydrogen peroxide is added on about a 0.25:1.0 mol equivalent basis with the amine. In exemplary procedures, an excess of alkyl nitrite, e.g., pentyl nitrite, or an excess of or at least a 1:1 molar equivalent of $NaNO_2$ in up to about a 20 fold excess of mineral acid (usually HCl), is employed as the source of nitrous acid. While prior art procedures (see, e.g., Cadogan, op.cit.) often require that the reaction be conducted at the boiling point of the solvent, by the process of the present invention, reaction temperatures at or near room temperature and atmospheric pressures are employed, with concomitant ease of handling. The reaction mixture is typically stirred until the reaction is completed, generally for less than about one hour, and usually from about 15 to about 30 minutes. The product is easily worked up by evaporation of the solvent in vacuo and isolation by customary chromatographic or extraction procedures.

In an alternate embodiment of the invention, the amine $ArNH_2$ is diazotized in conventional manner with a source of nitrous acid, especially $NaNO_2$ in aqueous HCl. The resultant solution, if not to be used immediately, is chilled to stabilize the product diazonium salt, or, alternatively, the salt is converted to a more stable derivative such as a fluoborate salt or other comparable complex salt in a known manner. The diazonium salt is subsequently "reduced" to remove and replace the diazo group with a hydrogen ion. This "reduction" is accomplished by known prior art techniques which comprise reacting the diazonium salt with a suitable source of hydrogen. According to the process of the invention, however, $H_2O_2$ is added to the reduction reaction in amounts sufficient to provide at least about 0.25:1 molar equivalent of $H_2O_2$ and diazonium salt. Solvents other than THF or dioxane may be employed.

It will be appreciated by those skilled in the art that a variety of replacement reactions involving the diazo group are comparable to the described hydrogen replacement reaction, and it is contemplated that $H_2O_2$ according to the invention may effectively promote such reactions. Potentially applicable reactions include replacement of the diazo group with cyano, hydroxy, or halo (Sandmeyer) groups, employing the appropriate reactants.

EXAMPLES

The following examples are illustrative of the practice of the invention:

EXAMPLE I

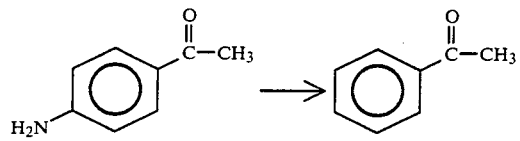

A solution of 0.133 g (0.985 mmol) of p-aminoacetophenone in 25 ml of 9:1 dioxane-acetic acid was cooled to 0° at which time 6.02 ml of 2N HCl was added. After 5 min 0.29 ml of 3% $H_2O_2$ was added followed by the addition of 68 mg (1.0 mmol) of $NaNO_2$ in 1.8 ml of water. The evolution of nitrogen from the reaction mixture was observed immediately. The reaction mixture was allowed to stir at 0° C. for 10 min and 25° C. for 15 min. The crude yellow mixture was poured into 25 ml of 10% KOH solution and extracted with ethyl ether (3×15 ml). The organic layer was washed with 5% $NaHCO_3$ (2×15 ml), water (2×15 ml) and dried over anhydrous $MgSO_4$. Removal of the solvents under reduced pressure gave a near quantitative yield of an oil which was identical to standard acetophenone in all respects.

EXAMPLES II, III AND IV 4-bromo-1-methylaniline (2); p-aminobenzoic acid (3); and 4-amino-1-bromoestradiol-3-methyl ether (4) and 4-aminoestradiol-3-methyl ether (5) were deaminated by the procedure of Example I with comparable results.

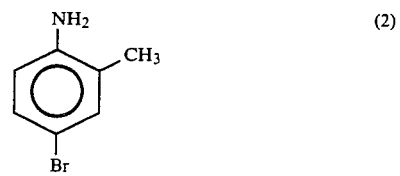

(2)

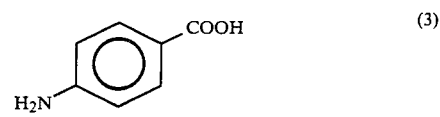

(3)

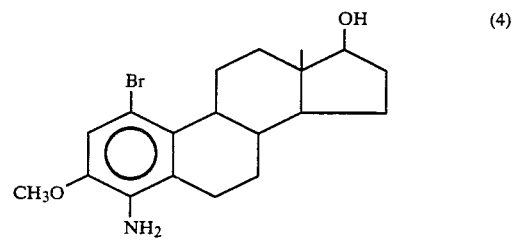

(4)

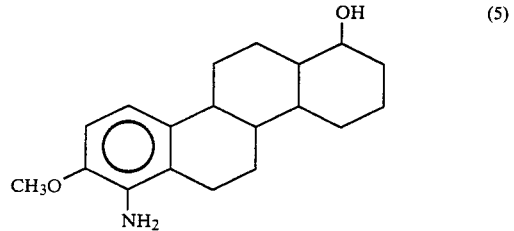

(5)

What is claimed is:

1. In a process for deaminating an aromatic primary amine of the type wherein the amino group is diazotized to form a diazonium salt and the diazo group of the diazonium salt is replaced with a replacement group, the improvement comprising deaminating the amine in the presence of hydrogen peroxide in an amount of at least about 0.25 mol peroxide per mol of diazonium salt.

2. The process of claim 1, wherein the diazo group is replaced by hydrogen.

3. The process of claim 2, wherein the aryl moiety of the aeromatic amine is substituted with alkyl, hydroxyl, acyl, carboxyl, halo, alkoxy, nitro, or phenyl.

4. The process of claim 3, wherein the aromatic amine is an amine of the formula $ArNH_2$, and Ar is phenyl, naphthyl, anthraquinoyl, or Ar is a steroid aromatic ring.

5. The process of claim 4, wherein the Ar is unsubstituent or substituted phenyl.

6. The process of claim 5, wherein Ar is substituent with carboxyl, hydroxyl, acyl, phenyl, alkyl, halo, nitro, or alkoxy.

7. The process of claim 4, wherein Ar is a steroid aromatic ring substituted with halo, alkoxy, or hydroxy.

8. In a process for the removal of the diazo or derivatized diazo group of an aromatic diazonium salt of the type wherein the diazo group or derivatized diazo group of the diazonium salt is replaced with a replacement group by reaction of the diazonium salt with a replacement group donor, the improvement comprising reacting the diazonium salt with a replacement group donor in the presence of $H_2O_2$ in an amount of at least about 0.25 mol $H_2O_2$ per mol diazonium salt.

9. The process of claim 8, wherein the replacement group is hydrogen.

10. The process of claim 9, wherein the hydrogen donor is tetrahydrofuran or dioxane.

11. The process of claim 1, wherein the replacement group is cyano, hydroxy or halo.

12. The process of claim 1, wherein the hydrogen peroxide is present in an amount of from at least about 0.25 to less than about 1 mol peroxide per mol diazonium salt.

13. The process of claim 2, wherein the diazonium salt is formed by reacting the aromatic amine with $NaNO_2$ in a mineral acid or with a lower $C_1$–$C_{10}$-alkyl nitrite.

14. The process of claim 13, wherein the aromatic amine is reacted with $NaNO_2$ in HCl or $H_2SO_4$.

15. The process of claim 2, wherein tetrahydrofuran or dioxane is employed in the process as the source of the hydrogen.

16. The process of claim 15, wherein the diazonium salt is formed by reacting the aromatic amine with an excess of alkyl nitrite, or with at least a molar equivalent nitrite, or with at least a molar equivalent of $NaNO_2$ in an up to about a 20-fold excess of mineral acid.

17. The process of claim 16, wherein the aromatic amine comprises an amine of the formula $ArNH_2$, wherein Ar is phenyl, biphenyl, anthraquinonyl, naphthyl, thiazolyl, pyridyl, pyrrolyl, quinoyl, or a steroid aromatic ring.

18. The process of claim 17, wherein Ar has at least one substituent in addition to —$NH_2$.

19. The process of claim 2, wherein the temperature of the reaction is at or near room temperature.

20. The process of claim 2, wherein the amine is deaminated in less than about one hour.

21. The process of claim 17, wherein the diazo group is replaced by hydrogen.

22. The process of claim 21, wherein tetrahydrofuran or dioxane is the source of the hydrogen.

23. The process of claim 22, wherein the diazonium salt is formed by reaction of the amine with $NaNO_2$ in a mineral acid or with a $C_1$–$C_{10}$-alkyl nitrite.

* * * * *